United States Patent [19]

Billings et al.

[11] Patent Number: 5,713,351
[45] Date of Patent: Feb. 3, 1998

[54] INTRAUTERINE MECONIUM DETECTION SYSTEM

[75] Inventors: R. Gail Billings, Salt Lake City; Roger E. Smith, Bountiful, both of Utah

[73] Assignee: Utah Medical Products, Inc., Midvale, Utah

[21] Appl. No.: 559,620

[22] Filed: Nov. 20, 1995

[51] Int. Cl.$^6$ ..................................................... A61B 5/00
[52] U.S. Cl. ........................... 128/632; 128/768; 128/775
[58] Field of Search ............................... 128/760, 768, 128/769, 770, 771, 775, 632, 634

[56] References Cited

U.S. PATENT DOCUMENTS

| | | | |
|---|---|---|---|
| 5,009,507 | 4/1991 | Katz | 356/421 |
| 5,361,759 | 11/1994 | Genevier et al. | 128/634 |
| 5,566,680 | 10/1996 | Urion et al. | 128/775 |

*Primary Examiner*—Jennifer Bahr
*Assistant Examiner*—Eric F. Winakur

*Attorney, Agent, or Firm*—Thorpe, North & Western, L.L.P.

[57] ABSTRACT

A system for intrauterine detection of one or more biological substances, such as meconium or blood, is described. The presence in amniotic fluid of such biological substances indicates an abnormal condition which justifies intervention on the part of a medical practitioner supervising the labor and delivery. A flexible cable which can be inserted into the uterus is provided which includes at least two lumens. The first lumen is used to draw amniotic fluid through the lumen into an observation chamber outside of the uterus and at the an end of the first lumen. The fluid is visually observed by a medical practitioner for the presence of a biological substance or the biological substance can be detected by any one several described instruments. It is preferred that if an instrument is used to detect the biological substance that a transparent visual observation chamber also be included so allow visual detection also. The apparatus allows stained fluid to be withdrawn from, and clean fluid to be infused into, the uterus in order to reduce the concentration of, and the effect of, the undesirable biological substance in the uterus.

45 Claims, 7 Drawing Sheets

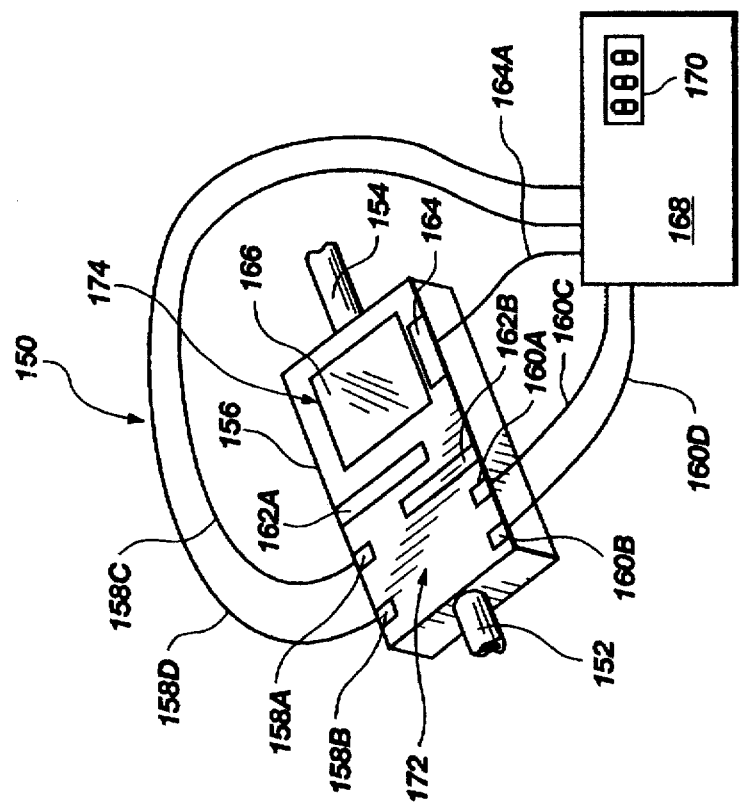
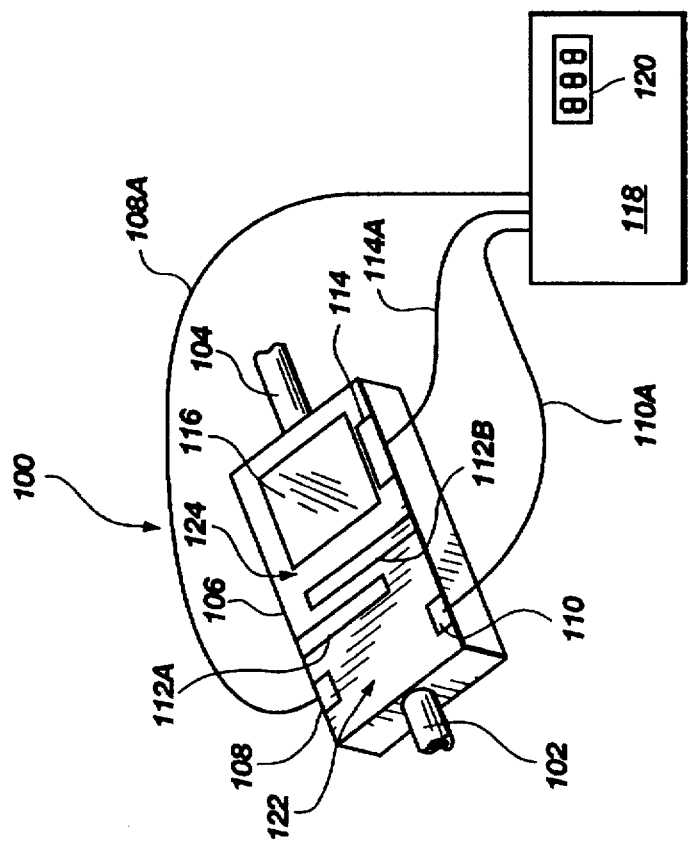
Fig. 4
Fig. 3

INTRAUTERINE MECONIUM DETECTION SYSTEM

BACKGROUND

1. The Field of the Invention

This invention relates to devices and methods used in the field of obstetrics and gynecology and more particularly to devices and methods used to monitor uterine conditions during labor and delivery.

2. The Background Art

During development of a human fetus, various biological materials, such as mucus, bile, and epithelial cells, accumulate in the colon of the fetus. Such materials accumulated in the fetus intestinal tract are referred to as meconium.

Generally, the fetus expels the accumulated meconium during the days following parturition. Undesirably, a fetus may pass meconium into the amniotic fluid before or during birth. For example, a stressful birth may cause the fetus to pass meconium into the amniotic fluid during labor and delivery.

Passing of meconium prior to birth causes much of the material to be suspended in the amniotic fluid. The presence of meconium in the amniotic fluid darkens the fluid and is thus referred to as "meconium staining" of the amniotic fluid.

Importantly, infants born with meconium staining generally have been shown to exhibit lower overall infant assessment (APGAR) scores than infants born without meconium staining. Critically, if meconium passes into the amniotic fluid before birth or during labor, there is a significant risk of the infant inhaling meconium into its lungs. Inhaling meconium during delivery results in a condition often referred to as "Meconium Aspiration Syndrome" (MAS), which is often manifest as a very severe form of pneumonia that can kill the infant or compromise pulmonary function for life. The aspiration of meconium may be a life threatening problem for as many as ten to twenty infants out of every ten thousand infants born.

In order to make medical decisions which might help to avoid MAS, the medical practitioner, for example an obstetrician or a pediatrician, would like to know early in the labor and delivery process the extent of meconium staining which has occurred. If the medical practitioner is able to determine early in the labor and delivery process that a dangerous degree of meconium aspiration is likely to occur, intervening steps can be taken to avoid harm therefrom, for example, sectioning of the newborn's pharynx to remove meconium, intubating the newborn's lungs to remove meconium or, in an extreme case delivering the fetus via cesarean section.

With the recognition of MAS as a serious concern, medical practitioners have in some instances begun to note meconium staining by direct visualization of the amniotic fluid, for example by noting the darkness or color of the amniotic fluid on a section of white linen. Unfortunately, waiting to observe meconium staining until sufficient amniotic fluid has drained onto linen may take too long to allow beneficial intervening action to be taken.

In order to provide a conservative procedure to detect meconium staining before and during the labor process, some have proposed to utilize intrauterine probes which are intended to determine the amount of meconium staining without obtaining a sample of the amniotic fluid. Such previously proposed devices have several drawbacks. One drawback is that they are expensive single use devices which generally serve no other purpose than the detection of meconium staining. Further, such previously available devices often require the insertion of photo emitter and photo detector devices into the uterus or the insertion of a fiber optic probe into the uterus. Moreover, such previously available devices can lack discrimination to detect meconium when vernix (a waxy substance which covers the fetus) or blood is also present in the amniotic fluid.

In view of the forgoing, it would be an advance in the art to provide a device which accurately detects meconium staining of amniotic fluid during labor and delivery procedures while avoiding the need to introduce additional devices into the uterus.

OBJECTS AND BRIEF SUMMARY OF THE INVENTION

In view of the above described state of the art, the present invention seeks to realize the following objects and advantages.

It is an object of the present invention to provide a system for detection of the presence and concentration of meconium in amniotic fluid during labor and delivery procedures.

It is an additional object of the present invention to provide a system for detection of one or more biological substances in amniotic fluid, for example blood and meconium, during labor and delivery procedures.

It is another object of the present invention to provide a system for both detection of meconium in amniotic fluid and measurement of intrauterine pressure during labor and delivery.

It is a further object of the present invention to provide a system and method for detecting meconium staining of amniotic fluid which is inexpensive and easy to use.

It is yet another object of the present invention to provide a system for detection of meconium staining of amniotic fluid which provides both visual and automated detection of meconium.

It is a further object of the present invention to provide a system for detecting meconium staining of amniotic fluid which is sufficiently convenient and inexpensive to use that it can be routinely employed in all deliveries.

It is yet a further object of the present invention to provide a system for detecting meconium in amniotic fluid during labor and delivery which can also measure one or more additional fetal or maternal physiological parameters.

It is still another object of the present invention to provide a system and method for intrauterine detection of meconium in combination with means for amnioinfusion of an externally provided fluid to dilute the amniotic fluid, the detection and amnioinfusion functions being provided by a single device.

It is yet another object of the present invention to provide a system and method for intrauterine detection of meconium in combination with means for withdrawing fluid from the uterus, both functions being provided by a single device.

These and other objects and advantages of the invention will become more fully apparent from the description and claims which follow, or may be learned by the practice of the invention.

The present invention provides a system for intrauterine detection of one or more biological substances, such as meconium and blood, whose presence in amniotic fluid indicates an abnormal condition which justifies intervention on the part of a medical practitioner supervising the labor of the mother and delivery of the infant.

In its preferred embodiments, the present invention includes a means for providing at least a first lumen, the first lumen having a first port located at a distal end of the lumen. A means for inserting the first port into the uterus can preferably comprise a flexible cable-like structure which can readily be inserted into the uterus.

A syringe in fluid communication with the first lumen and positioned at the proximal end of the first lumen is provided. The syringe is the preferable means for drawing fluid from the uterus into the first port and into the first lumen. At the proximal end of the first lumen is a means for observing the fluid such that the presence of a biological substance, such as meconium staining of the fluid, can be detected. In accordance with a further aspect of the present invention, an externally provided fluid, such as saline solution, can be infused into the uterus through the first lumen, or another lumen provided on the apparatus, to decrease the concentration of meconium. In accordance with yet another aspect of the present invention, fluid can be removed and infused through one or more lumens provided on the apparatus.

The means for observing the fluid drawn up into the first lumen can preferably comprise a transparent cuvette in fluid communication with the first lumen. The means for observing the fluid drawn up into the first lumen can also comprise a means for holding a volume of the fluid and a viewing means for visually observing the appearance of the fluid and means for illuminating the interior of the means for holding such that at least any threshold amount of meconium present in the fluid can be observed. A color reference scale or color patches can also preferably be included to assist with visually detecting meconium or visually detecting some other biological substance, such as blood.

The means for observing the fluid can also preferably comprise means for holding the fluid with means for visually observing the appearance of the fluid in combination with structures for instrumentally detecting a biological substance. Structures for instrumentally detecting a biological substance can preferably include photo emitter and photo detector means, fluorescence emitter and florescence detector means, processing means, and means for indicating in a humanly perceptible manner the detection of meconium or some other biological substance in the amniotic fluid.

In accordance with another aspect of the present invention, a pressure transducer is provided adjacent to the distal end of the first lumen. The pressure transducer resides in the uterus and detects the pressure in the uterus during labor and delivery. A protective cushion means is positioned over the pressure transducer and a means for imparting a desired degree of rigidity to the apparatus inserted into the uterus is provided to facilitate insertion into the uterus.

The pressure transducer includes a diaphragm and a pressure transmitting substance acts as a means for communicating any pressure pulses from the fluid in the uterus to a first side of the diaphragm. A second lumen preferably functions as a means for venting the second side of said diaphragm to atmospheric pressure is also provided to ensure accurate pressure detection within the uterus. Electrical conductors preferably function as electrical conductor means for electrically connecting the pressure transducer to a monitor device for displaying data corresponding to pressure sensed by the pressure transducer.

The present invention also provides a corresponding method for intrauterine detection of a selected biological substance including the steps of: providing at least a first lumen, the first lumen having a first port located at a distal end of the lumen; inserting the first port into a uterus; drawing fluid from the uterus into the first port into the first lumen; and observing the fluid drawn up the lumen such that a biological substance in the fluid can be detected.

BRIEF DESCRIPTION OF THE DRAWINGS

In order to better appreciate how the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 3 is a detailed perspective view of another amniotic fluid observation arrangement included in a second embodiment of the present invention, FIG. 4 is a detailed perspective view of another amniotic fluid observation arrangement included in a third embodiment of the present invention.

DETAILED DESCRIPTION OF THE PREFERRED EMBODIMENTS

Reference will now be made to the drawings wherein like structures will be provided with like reference designations.

Figure 1:
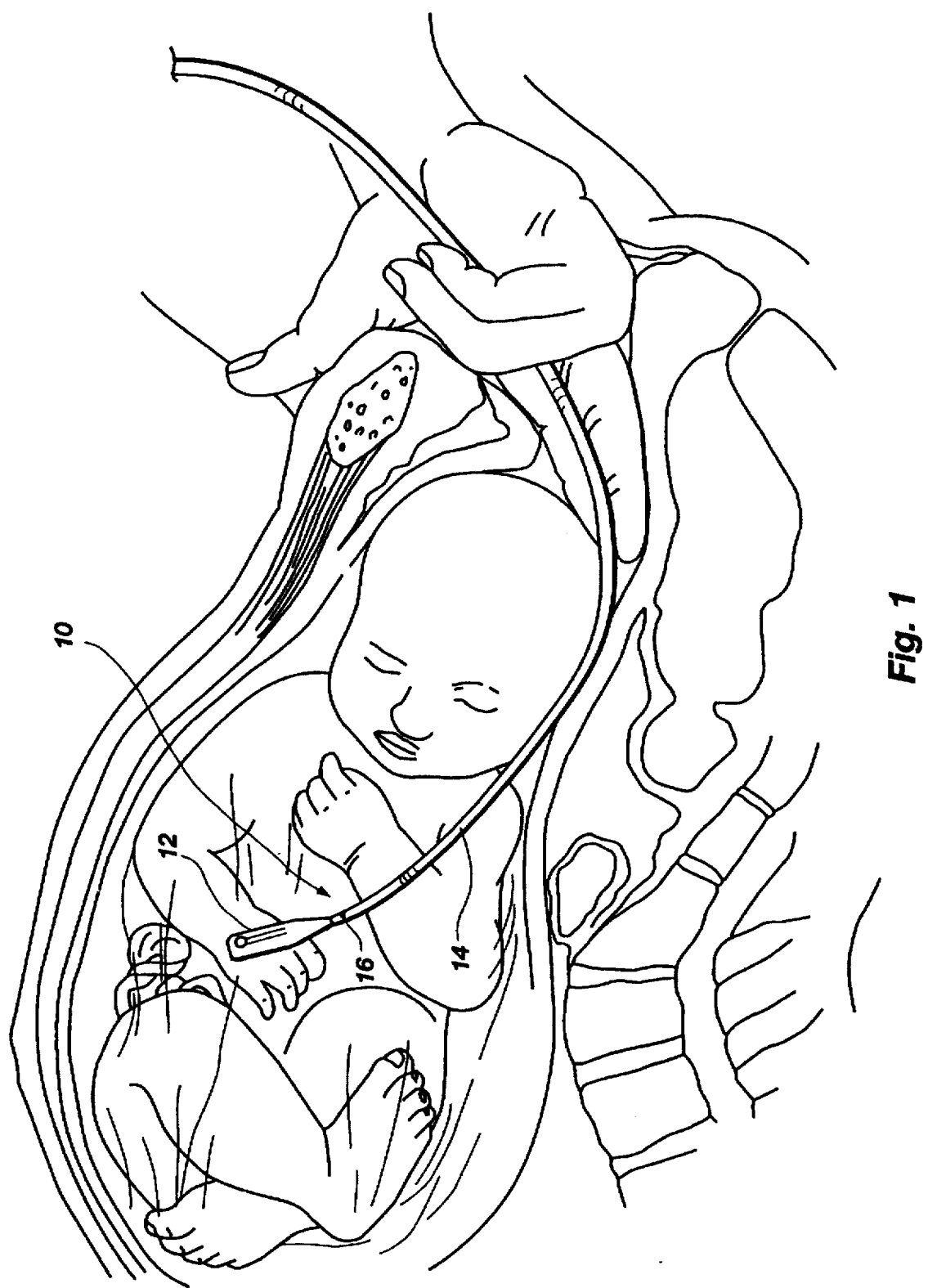
FIG. 1 is a partially cut away perspective view illustrating placement of an embodiment of the present invention within a uterus during childbirth.

Referring first to FIG. 1, the use of a first presently preferred embodiment of the present invention is illustrated. As discussed above, the problem of providing a medical practitioner information on meconium or blood staining early in the labor and delivery process has either not been recognized in the industry or has not be adequately solved prior to the advent of the present invention.

FIG. 1 is a partial cross sectional view of a uterus and fetus wherein a cable assembly, generally indicated at 10, of the first presently preferred embodiment is introduced into the uterus to provide monitoring of both intrauterine pressure and meconium staining of the amniotic fluid. As will be understood in the art, the patient should be in the dorsal lithotomy position, the uterine membrane ruptured, and the cervix adequately dilated before insertion of the cable assembly 10. Using the hand and fingers as shown to guide the cable assembly 10, it is inserted into the cervix until it is well into the amniotic space. Insertion should be performed carefully and gently, without force. Any cervical quadrant may be used.

In accordance with the present invention, an introducer structure (not illustrated in the figures) may be used to guide the cable assembly into position in the uterus. The cable assembly can also be fabricated with sufficient stiffness to allow the cable assembly 10 to be positioned into the uterus past the head of the fetus while manipulating the apparatus from outside the uterus.

The cable assembly 10 of the embodiment represented in FIG. 1 includes a cable 14 which is provided with, at its distal end, a boot 12 which houses pressure sensing components and a distal port 16 through which amniotic fluid can be sampled. Also, one or more insertion marks 18 can desirably be provided at selected positions along the cable 14. Further information regarding these structures will be given shortly. While the represented embodiment advantageously provides both meconium staining detection as well as intrauterine pressure monitoring, it will be appreciated that embodiments of the present invention can provide biological substance detection in combination with other physiological parameters, such as fetal heart rate, maternal heart rate, or sampling of and infusion into the amniotic fluid, and so forth as will be recognized by those skilled in the art.

Figure 2:
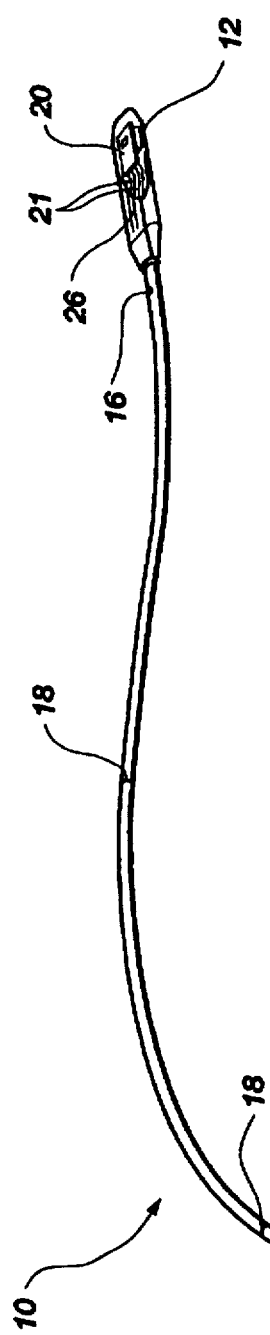
FIG. 2 is a perspective view of a first presently preferred embodiment of the present invention.
Figure 2:
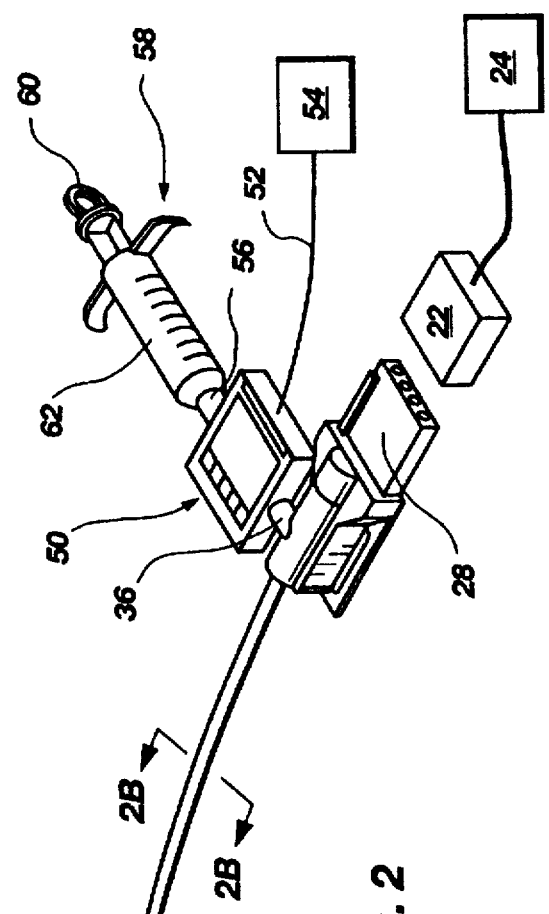

Reference will next be made to FIG. 2 which is a perspective view of the first presently preferred embodiment of the present invention. Illustrated in FIG. 2 is the cable assembly 10 with the boot 12 and the distal port 16. As illustrated, the boot 12 is provided with a hole 20 which communicates with the pressure sensing components (represented at 21) contained in the boot 12. The hole 20 is preferably filled with suitable pressure transmitting substance which functions to isolate the pressure sensing components 21 from the surrounding environment. Advantageously, in order to prevent fluids or tissue from obstructing the hole 20 and thus interfering with the pressure measurements, the boot 12 may be provided with a plurality of grooves 26 surrounding the hole 20, as illustrated in FIG. 2.

The cable 14 extends from the boot 12 and includes conductors (illustrated in FIG. 2B) which carry electrical signals from the pressure sensing components. The electrical signals represent the pressure within the uterus and are conveyed to a plug 28 which is connected to a reusable receptacle 22 leading to a monitor 24, such that the pressure data may be appropriately displayed and/or recorded by the monitor. For example, a plug represented at 22 leads to a monitor 24 such as can be devised by those skilled in the art or which are available in the industry.

Presently preferred arrangements for providing the pressure sensing components included in the cable assembly are described in U.S. Pat. No. 4,610,256 entitled PRESSURE TRANSDUCER, U.S. Pat. No. 4,873,986 entitled DISPOSABLE APPARATUS FOR MONITORING INTRAUTERINE PRESSURE AND FETAL HEART RATE, and U.S. Pat. No. 4,785,822, entitled DISPOSABLE INTRACOMPARTMENTAL PRESSURE TRANSDUCER, all of which are now incorporated herein by reference in their entireties.

Figures 2A, 2B:
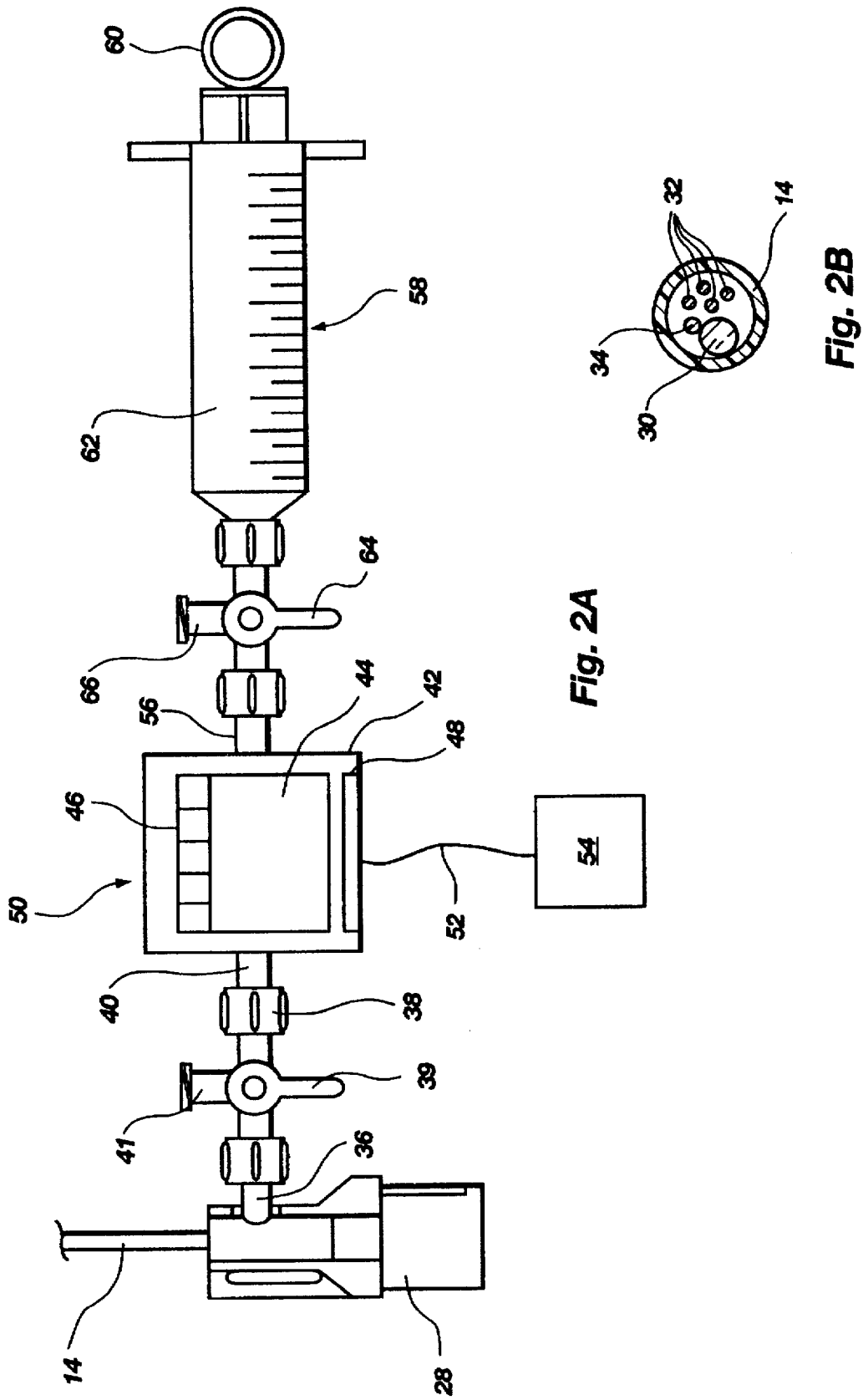
FIG. 2A is a detailed view of the amniotic fluid observation arrangement included in the first embodiment of the present invention.
FIG. 2B is a cross sectional view of the cable assembly taken along line 2B—2B of FIG. 2.

Reference will next be made to FIGS. 2A and 2B to explain the preferred structures used to provide detection of biological substances in the amniotic fluid, including meconium staining of amniotic fluid. FIG. 2B is a cross sectional view of the cable 14 taken along line 2B—2B of FIG. 2. FIG. 2B illustrates insulated conductors 32 which are exemplary of one preferred structure used to convey signals generated by the pressure sensing components housed in the boot 12. The conductors 32 may be any suitable electrical conductors available in the art. Moreover, any media now available in the industry, or which may become available in the future, may also be suitably used to convey signals which are generated by the components located at the distal end of the cable assembly 10.

As explained in the publications previously incorporated herein by reference, in order to obtain accurate intrauterine pressure measurements, the pressure readings of transducer apparatus 10 should be referenced to some substantially constant reference pressure. The reference pressure is conveyed by a vent lumen 34 which normally leads to atmospheric pressure as explained in the earlier referenced publications. The vent lumen 34 can also be used to calibrate the pressure detection components 21. For example, a vacuum can be imposed through vent lumen 34 to perform any necessary calibration.

It is within the scope of the present invention to also provide pressure deduction devices at the proximal end of the cable assembly 10 and the pressure within the uterus conveyed to the pressure detection device via a column of fluid held by a lumen provided within the cable assembly 10. As shown best in FIG. 2B, a fluid lumen 30 is provided within the cable assembly 10. The fluid lumen 30 allows fluid communication between the distal port 16 and a proximal port 36 which is in fluid communication with the fluid lumen 30. With the cable assembly 10 inserted into the uterus as represented in FIG. 1, the distal port 16 is in contact with amniotic fluid and amniotic fluid can be draw up into the fluid lumen (30 in FIG. 2B) of the cable assembly 10. It will be appreciated that the proximal port 36 can be positioned in any appropriate location along the cable 14 but is preferred to be located in the position illustrated on the plug 28.

FIG. 2A provides a detailed view of a visual observation chamber, generally designated at 50, which provides visual detection of a biological substance, such as meconium staining, in amniotic fluid. The cable 14 is provided with the proximal port 36 which is connected to the fluid lumen (30 in FIG. 2B). Thus, a fluid coupling is provided between the distal port (16 in FIG. 2) and the proximal port 36 allowing any fluid present in the uterus at the distal port 16 to be drawn up to the proximal port 36.

The proximal port 36 is preferably provided with a diverter valve 39 which selectively connects the proximal port 36 to a port 41. The port 41 can preferably be used to divert fluids contained in the fluid lumen (30 in FIG. 2B) to the port 41 for collecting samples in a collection device. Alternatively, fluids may be infused into the fluid lumen (30 in FIG. 2B) through the port 41 as may be desired by a medical practitioner during labor and delivery.

The diverter valve 39 can also divert fluid into the visual observation chamber 50 by way of an inlet 40 provided on the visual observation chamber 50 and which is preferably attached to the diverter valve 39 via a Luer-type connector 38 such as is known in the industry. The visual observation chamber 50 is preferably fabricated from a transparent material and includes a cuvette 42.

An outlet 56 on the observation chamber is connected to a syringe, generally indicated at 58. The syringe 58 is one preferred arrangement for drawing fluid from the uterus into the fluid lumen (30 in FIG. 2B) and up into the visual observation chamber 50. The syringe 58 includes a syringe body 62 which is preferably provided with volume markings as known in the art. A grasping loop 60 is preferably provided on the end of the syringe plunger 60 to allow the medical practitioner to readily aspirate fluid into the visual observation chamber 50.

A diverter valve 64 is connected in the fluid path between the visual observation chamber 50 and the syringe 58. When in a first position, the diverter valve 64 provides a fluid path between the visual observation chamber 50 and the syringe 58 so that amniotic fluid can be readily drawn up into the visual observation chamber 50. When in a second position, the diverter valve 64 provides a fluid path between the syringe 58 and a port 66 to allow the contents of the syringe to be expelled, and if desired, so that additional fluid can be drawn into the visual observation chamber 50.

The cuvette 42 is preferably fabricated to have optical properties allowing a practitioner to accurately observe the color and turbidity of the amniotic fluid aspirated therein. Provided within the cuvette 42 is a background plate 44 which is positioned and colored to improve the ability of a practitioner to detect the presence and concentration of meconium, or other biological substances, in the amniotic fluid. An optical scale 46 is also preferably provided. The optical scale 46 can preferably be a grey scale, a color scale, or a combination of both types of scales. It is within the scope of the present invention to provide detection of, and optical scales for, blood as well as meconium.

An illumination device 48 is connected to a power source 54, such as a battery, via a cord 52. The illumination device 48 can comprise a number of different devices known in the industry, such as an incandescent lamp, and can include a filter to provide an illumination spectrum which is best suited for visually detecting meconium in amniotic fluid.

In use, a practitioner inserts the cable assembly 10 in the uterus as illustrated in FIG. 1 and as represented in FIG. 2 the plug 28 is received by a receptacle 22 so that pressure detected in the uterus can be displayed on the monitor 24. Early on in the labor and delivery process the diverter valves 39 and 64 are positioned to provide a fluid path from the distal port 16 (FIG. 2) through the fluid lumen 30 (FIG. 2B) and the visual observation chamber 50 (FIG. 2A) into the syringe 58. Amniotic fluid is aspirated up into the visual observation chamber 50 and the practitioner visually observes the condition of the amniotic fluid for meconium or other biological substances. If actionable concentrations of meconium are detected, the practitioner can take appropriate steps.

Such appropriate interventional steps can include, in accordance with the present invention, infusion of additional fluid into the uterus through the fluid lumen (30 in FIG. 2B) or through another lumen or fluid path provided into the uterus. The infusion of additional fluid into the uterus lowers the concentration of any meconium which is present and reduces the amount of meconium which is likely to be aspirated by the fetus. It is also within the scope of the present invention to withdraw fluid from the uterus using one of the fluid paths provided by the apparatus and to infuse meconium-free fluid into the uterus to reduce the concentration of meconium present in the uterine fluid. Those skilled in the art will appreciate that a single lumen, for example fluid lumen 30 in FIG. 2B, can be used to alternately withdraw fluid from, and infuse fluid into, the uterus. Alternatively, the apparatus of the present invention can include additional fluid lumens so that the withdrawal of fluid from the uterus and the infusion of fluid into the uterus can occur simultaneously. It will be appreciated that the location of the distal ports connected to lumens used for withdrawal and infusion of fluid along the cable (14 in FIG. 1) can be chosen for most efficient removal of meconium stained fluid and infusion of clean fluid into the uterus. Amnioinfusion, either alone or used in conjunction with withdrawal of fluid from the uterus, is effective in reducing the effect of an undesirable biological substance, such as meconium, in the uterus.

Reference will next be made to FIG. 3 to describe a densitometer observation chamber 100 which can be used as an alternative to the visual observation chamber 50 represented in FIGS. 2 and 2A. An inlet 102 is connected to the proximal port (36 in FIG. 2) to provide a fluid path to the fluid lumen leading to the uterus. An outlet 104 is preferably connected to a device for drawing fluid from the uterus, such as the syringe 58 represented in FIGS. 2 and 2A.

Advantageously, the densitometer observation chamber 100 provides for both visual detection of meconium in the aspirated fluid and for instrumental measurement of meconium concentrations using densitometric techniques. A cuvette 106 is provided with an opaque portion, generally indicated at 122, and a transparent portion, generally indicated at 124. A photo emitter 108 is provided internal to the cuvette 106 in the opaque portion 122. A photo detector 110 is also provided internal to the cuvette 106. The photo emitter 108 and the photo detector 110 are connected to a monitor 118 by way of cables, 108A and 110A, respectively.

The photo emitter 108 and the photo detector 110 are positioned in the opaque portion 122 of the cuvette 106 so that when the cuvette is filled with fluid the optimum amount of fluid is interposed between the photo emitter 108 and the photo detector 110 after the practitioner has aspirated fluid into the densitometer observation chamber 100. The photo emitter 108 and the photo detector 110 can be arranged so that the photo detector receives transmitted light, as positioned in FIG. 3, or arranged so that the photo detector 110 receives reflected or scattered light. The photo emitter 108 and the photo detector 110 are preferably selected from those available in the art and are isolated to provide any necessary protection from the fluid drawn into the cuvette 106. The opaque portion 122 of the cuvette 106 is provided to shield the photo detector 110 from ambient light. A plurality of baffles 112A & B are also provided internal to the cuvette 106 to prevent ambient light from leaking through the cuvette 106 and reaching the photo detector 110.

The photo emitter 108 and the photo detector 110 are selected to utilize appropriate optical wavelengths. Since the composition of meconium will change from fetus to fetus the wavelengths used can desirably be broad enough to provide suitable detection. It is often the case that meconium absorbs emissions in the range from about 400 nanometers (nm) to about 420 nm and the photo emitter 108 and the photo detector 110 can be appropriately selected. The photo detector 110 generates a signal which is processed by the monitor 118 using either digital or analog techniques to show a corresponding value on the display 120.

In the transparent portion 124 of the cuvette 106 a background plate 116 and an illumination device 114, which is connected to the monitor 118 via a cable 114A, are both provided to assist with visual detection of meconium as described earlier.

Reference will next be made to FIG. 4 to describe a colorimeter observation chamber 150 which can be used as an alternative to the other observation arrangements represented in FIGS. 2 and 3. As shown in FIG. 4, an inlet 152 is connected to the proximal port (36 in FIG. 2) to provide a fluid path to the fluid lumen leading into the uterus. An outlet 154 is preferably connected to a device for drawing fluid from the uterus such as the syringe 58 represented in FIGS. 2 and 2A.

Advantageously, the colorimeter observation chamber 150 provides for both visual detection of meconium in the aspirated fluid and for making instrumental measurement of meconium concentrations using calorimetric techniques. A cuvette 156 is provided with an opaque portion, generally indicated at 172, and a transparent portion, generally indicated at 174. A pair of photo emitters 158A & B are provided internal to the cuvette 106 in the opaque portion 122. A pair of photo detectors 160A & B are also provided internal to the cuvette 156. The photo emitters 158A & B and the photo detectors 160A & B are connected to a monitor 168 by way of cables, 158C & D and 160C & D, respectively.

The photo emitters 158A & B and the photo detectors 160A & B are positioned in the opaque portion 172 of the cuvette 156 so that when the cuvette is filled with fluid the optimum amount of fluid is interposed between the photo emitters 158A & B and the photo detectors 160A & B after the practitioner has aspirated fluid into the colorimeter observation chamber 150. The photo emitters 158A & B and the photo detectors 160A & B can be arranged so that the photo detectors receive transmitted light, as positioned in FIG. 4, or arranged so that the photo detectors 160A & B receive reflected or scattered light. The photo emitters 158A & B and the photo detectors 160A & B are preferably selected from those available in the art and are housed to provide isolation and/or protection from the fluid drawn into the cuvette 156. The opaque portion 172 of the cuvette 156 is provided to shield the photo detectors 160A & B from ambient light. A plurality of baffles 162A & B are also provided internal to the cuvette 156 to prevent ambient light from leaking through the cuvette 156 and reaching the photo detectors 160A & B.

It will be appreciated that in some instances the aspirated fluid will be turbid, for example, due to the shedding and dispersion of vernix. In such instances, positioning the photo detectors 160A & B to receive reflected or scattered light from the photo emitters 158A & B can beneficially be carried out.

The photo emitters 158A & B and the photo detectors 160A & B are selected to utilize appropriate optical wavelengths. For example, the photo detectors 160A & B may be alternatively operated at two different wave lengths, for example a wavelength which meconium highly absorbs (about 400 to about 420 nm) and another wavelength which is not significantly absorbed by meconium (for example, about 500 nm). It is also within the scope of the present invention to emit and detect a wavelength which is absorbed by blood (for example, about 575 nm) in conjunction with wavelengths used for detection of meconium. If necessary, a third photo emitter and a third photo detector (not illustrated in the figures) can be added to provide suitable detection of two biological substances of interest (e.g. meconium and blood) in the amniotic fluid.

The photo detectors 158A & B can be selected from those wide band photo detectors available in the industry or may be selected to provide detection for the particular wavelengths emitted by the photo emitters 158A & B.

Alternatively, the photo emitters 158A & B can be wide band emitters with appropriate filters optionally being provided at the photo emitters 158A & B or at the photo detectors 160A & B. Importantly, since the composition of meconium will change from fetus to fetus, the wavelengths used should be broad enough to provide suitable detection.

The photo detectors 160A & B generate signals which are processed by the monitor 168 to show a corresponding value on the display 170. As will be appreciated by those skilled in the industry, the monitor preferably includes power supplies for the photo emitters 158A & B, amplifiers for the signals generated by the photo detectors 160A & B, analog-to-digital convertors, and a microprocessor which can be readily programmed using the information contained herein and in accordance with known techniques.

In the transparent portion 174 of the cuvette 156 a background plate 166 and an illumination device 164, which is connected to the monitor 168 via a cable 164A, and both are provided to assist with visual detection of meconium as described earlier.

Figure 5:
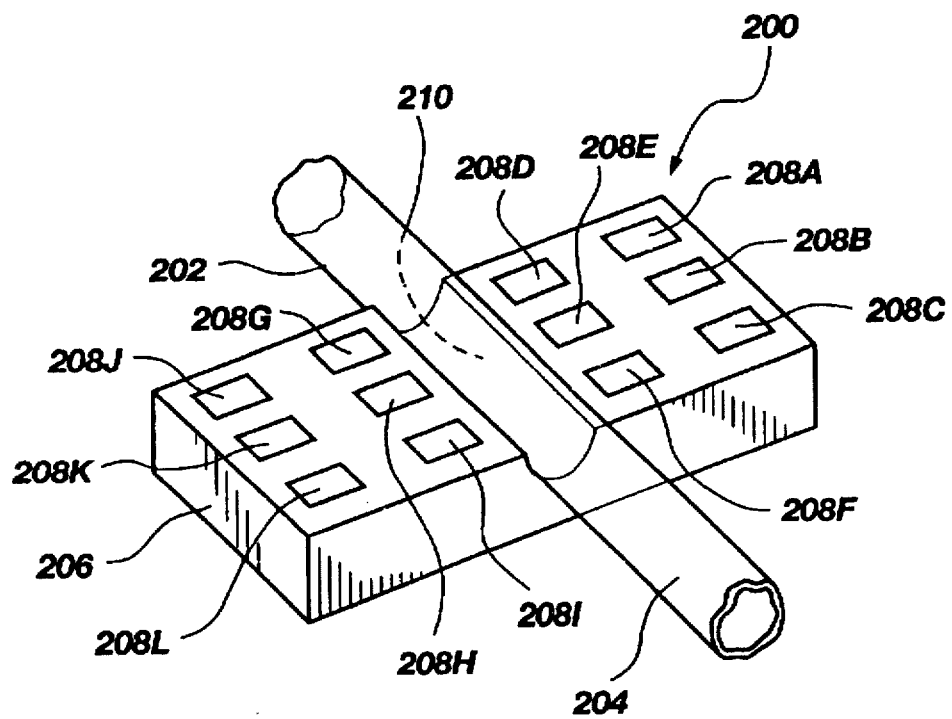
FIG. 5 is a detailed perspective view of another amniotic fluid observation arrangement included in a fourth embodiment of the present invention.

Reference will next be made to FIG. 5 to describe another observation arrangement 200 which can be used as an alternative to, or in conjunction with, the observation chambers represented in FIGS. 2, 3, and 4. As represented in FIG. 5, a transparent tube includes an inlet 202 which is preferably connected to the proximal port (36 in FIG. 2) to provide a fluid path to the fluid lumen leading into the uterus. The transparent tube also includes an outlet 204 which is preferably connected to a device for drawing fluid from the uterus such as the syringe 58 represented in FIGS. 2 and 2A.

Advantageously, a color reference block 206 is provided to assist the practitioner to make a visual determination of the meconium concentration, or the concentration of some other biological substance either alone or in combination with meconium, in the amniotic fluid. The color reference block 206 is preferably fabricated from a material which most beneficially assists the practitioner in making the visual determination. For example, it is presently preferred that the color reference block 206 be fabricated from a white plastic material. A channel 210 is formed in the color reference block 206 to closely receive the transparent tube containing the amniotic fluid. The transparent tube can be fixed to the color reference block 206 or the color reference block 206 can be moved from one patient to another and reused.

Provided on the upper surface of the color reference block 206 are color reference patches 208A–L. Each color reference patch 208A–L provides a hue, chroma, and intensity which corresponds to the visual appearance of a particular concentration of meconium, some other biological substance, or the combination of meconium and some other substance, in amniotic fluid. It will be appreciated that the number of color reference patches 208A–L provided on the color reference block 206 can be greater or fewer than those represented in FIG. 5. Moreover, the color reference patches 208A–L can each represent a different value of substance concentration or two or more color reference patches can be used to represent a particular substance concentration as may be desirable to assist the practitioner when visually determining the concentration. It is to be understood that the observation arrangement 200 can be used alone or together with other concentration detection arrangements.

When the tube is placed in the channel 210, the practitioner can make a visual match between the appearance of the amniotic fluid and the color reference patch 208A–L which best corresponds to the color of the amniotic fluid. Each of the color reference patches 208A–L is preferably provided with a legend (not represented in the figures) which provides a literal value (for example, numeric and/or alphabetic) corresponding to the concentration of the visually detectable biological substance(s) in the amniotic fluid.

Figure 6:
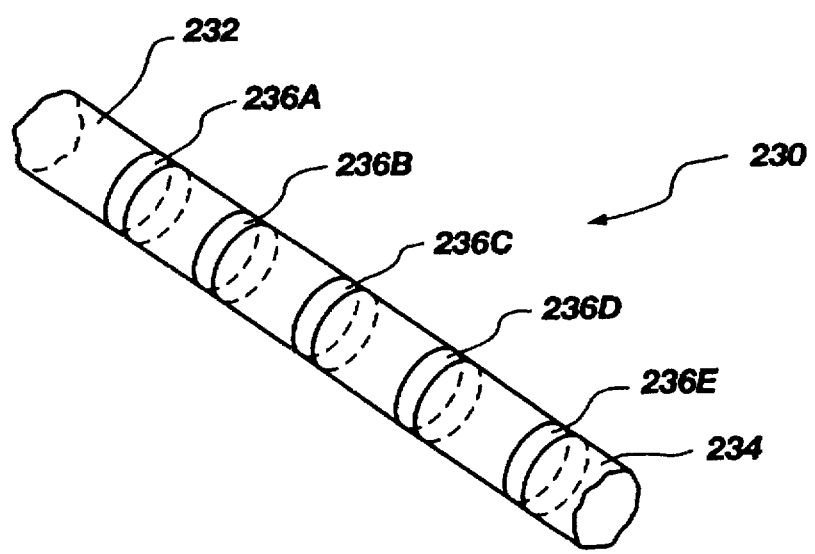
FIG. 6 is a detailed perspective view of still another amniotic fluid observation arrangement included in a fifth embodiment of the present invention.

Reference will next be made to FIG. 6 to describe an observation arrangement 230 which can also be used to make visual determinations of meconium and other biological substance concentrations in amniotic fluid. As represented in FIG. 6, a tube fabricated from a transparent material includes an inlet 232 and an outlet 234. The inlet 232 is preferably connected to the proximal port (36 in FIG. 2) to provide a fluid path to the fluid lumen leading into the uterus. The outlet 234 is preferably connected to a device for drawing fluid from the uterus such as the syringe 58 represented in FIGS. 2 and 2A.

Advantageously, color reference bands 236A–E are provided to assist the practitioner to make a visual determination of the meconium or other biological substance concentration in the amniotic fluid. Preferably, each of the color reference bands 236A–E provides a different color (as explained earlier) which corresponds to the visual appearance of a particular concentration in amniotic fluid. It will be appreciated that the number of color bands 236A–E provided between the inlet 232 and the outlet 234 can be greater or fewer than those represented in FIG. 6. Moreover, as with the other meconium observation arrangements described herein, the color bands 236A–E can be placed anywhere along the fluid path where visual observation of stained amniotic fluid is convenient. Each of the color bands 236A–E can represent a different value of substance concentration or two or more color reference patches can be used to represent a substance concentration if it assists the practitioner to visually determine the actual substance concentration.

In use, the practitioner makes a visual match between the appearance of the amniotic fluid and the color band 236A–E which best corresponds to the appearance of the amniotic fluid. Also, as described earlier, each of the color bands 236A–E is preferably provided with a legend (not represented in the figures) corresponding to the respective substance concentration.

Figure 7:
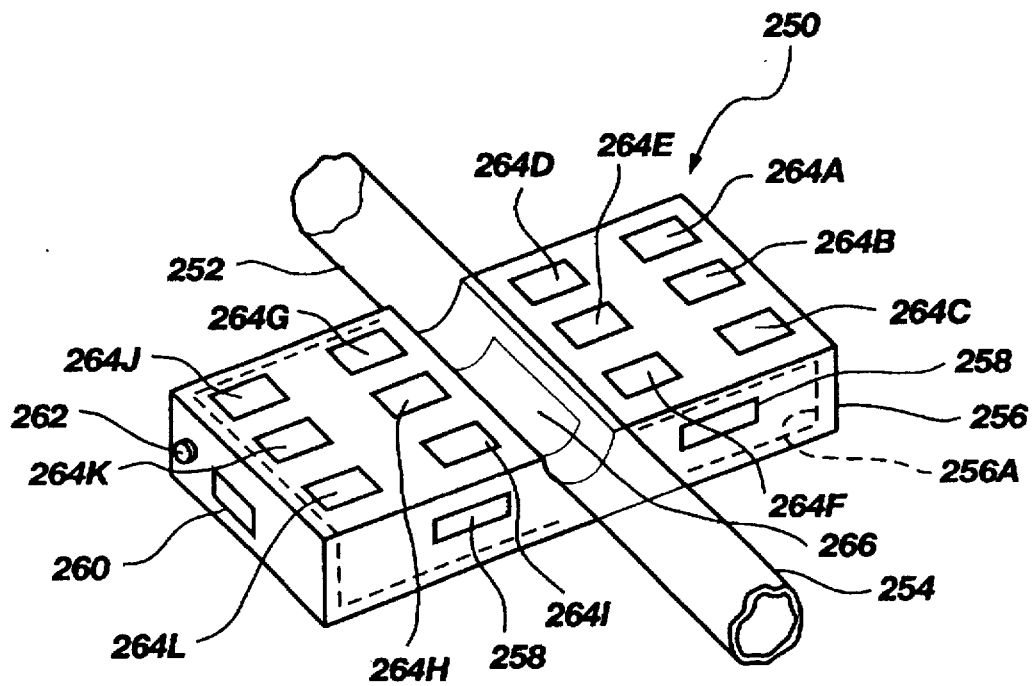
FIG. 7 is a detailed perspective view of yet another amniotic fluid observation arrangement included in a sixth embodiment of the present invention.

Reference will next be made to FIG. 7 to describe another observation arrangement 250 which can be used as an alternative to, or in conjunction with, the observation arrangements represented in FIGS. 2–6. Represented in FIG. 7 is a transparent tube which includes an inlet 252 (which is preferably connected to the proximal port 36 in FIG. 2) to provide a fluid path to the fluid lumen leading into the uterus and an outlet 254 which is preferably connected to a device for drawing fluid from the uterus such as the syringe 58 represented in FIGS. 2 and 2A.

In the observation arrangement 250 an illuminated color block 256 is provided to further assist the practitioner to make a visual determination of the substance concentration in the amniotic fluid which is present between the inlet 252 and the outlet 254. The illuminated color reference block 256 is preferably fabricated from an opaque plastic material with a hollow interior. Housed within the interior of the color reference block 256 are photo emitters 258 which can assembled from any of a number of components available in the industry. A power source 260, which can preferably be a battery, is connected to a switch 262 and the photo transmitters 258 so that the photo emitters are illuminated when the switch 262 is actuated.

A translucent window 266 is provided in a channel which receives the tube between the inlet 252 and outlet 254 thereof. When the switch 262 is actuated, the diffuse light transmitted through the translucent window 266 is transmitted into the tube. Moreover, a plurality of color reference patch windows 264A–L are formed in the upper surface of the illuminated color block 256. Each color reference patch window 264A–L is provided with a transparency which provides a color which corresponds to the visual appearance of a particular concentration of a substance or substances in amniotic fluid. The number of color reference patch windows 264A–L can be varied with each color reference patch window being dedicated to a different value of a substance concentration or two or more color reference patch windows can be used to represent a particular substance concentration, and the observation arrangement 250 can be used alone or together with other concentration detection arrangements. With both the amniotic fluid between the inlet 252 and the outlet 254 and the color transparencies provided in the color reference patch windows 264A–L being illuminated by the photo emitters 258, the practitioner is greatly assisted when making a visual match between the appearance of the amniotic fluid to the appropriate color found in the color reference patch windows 264A–L which best corresponds to the color of the amniotic fluid.

Figure 8:
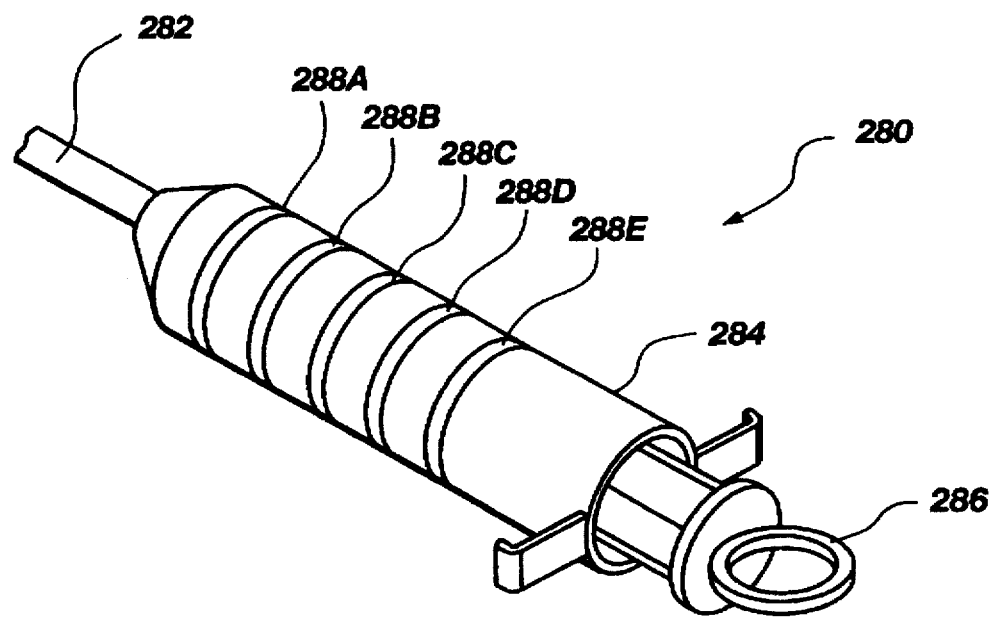
FIG. 8 is a detailed perspective view of a another amniotic fluid observation arrangement using a syringe which provides the function of amniotic fluid observation and which is included in a seventh embodiment of the present invention.

Reference will next be made to FIG. 8 which provides a detailed perspective view of another observation arrangement 280 which can be used as an alternative to, or in conjunction with, the observation chambers represented in the earlier figures. The observation arrangement 280 represented in FIG. 8 is intended to take the place of the device which draws fluid from the uterus and is preferably patterned after syringe 58 represented in FIGS. 2 and 2A. It is preferred that the syringe body 284 be fabricated from a transparent material. The inlet 282 provided on the syringe body 284 is preferably connected to the proximal port (36 in FIG. 2) to provide a fluid path to the fluid lumen leading into the uterus. As a syringe plunger 286 is withdrawn from the syringe body 284 the fluid is aspirated into the syringe body 284.

As the amniotic fluid collects in the syringe body 284, the practitioner compares the appearance of the fluid to the color bands 288A–E provided on the syringe body 284. The color bands can preferably be fabricated similarly to the color bands 236A–E described in connection with FIG. 6.

Figure 9:
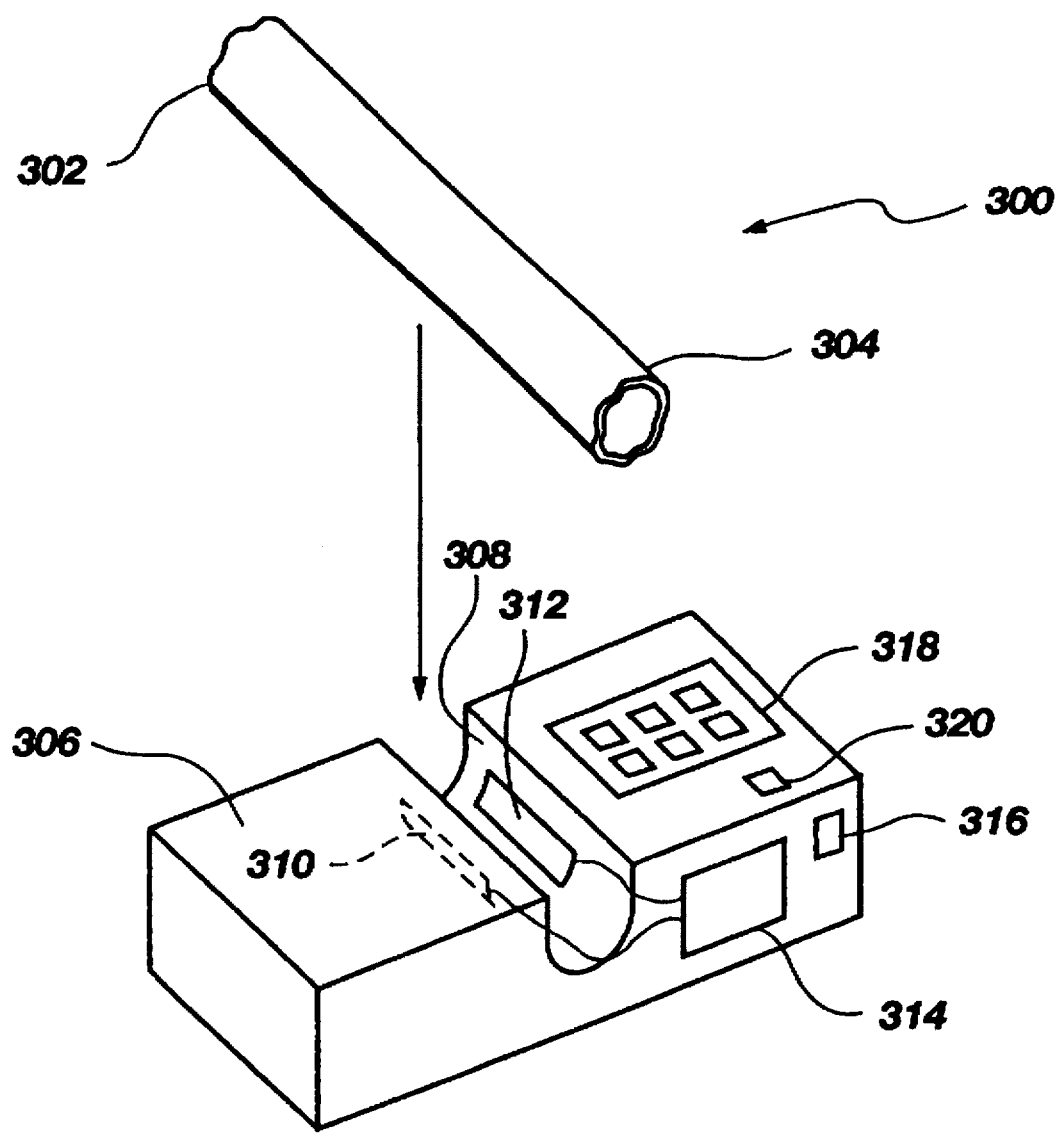
FIG. 9 is a detailed perspective view of a further amniotic fluid observation arrangement included in an eighth embodiment of the present invention.

FIG. 9 will be referred to next to describe another observation arrangement 300 which can be used as an alternative to, or in conjunction with, the observation arrangements represented in FIGS. 2–8. Represented in FIG. 9 is a transparent tube which includes an inlet 302 (which is preferably connected to the proximal port 36 in FIG. 2) to provide a fluid path to the fluid lumen leading into the uterus and also an outlet 304 which is preferably connected to a device for drawing fluid from the uterus (such as the syringe 58 represented in FIGS. 2 and 2A).

In the observation arrangement 300 represented in FIG. 9, a housing 306 contains a florescence detection system comprising a florescence emitter 310, a florescence detector 312, and a processor 314. The florescence emitter 310, florescence detector 312, and the processor 314 are merely diagrammatically represented in FIG. 9 and are preferably patterned after those available in the industry used to detect bilirubin but other components can also be used within the scope of the present invention. A power source 316, for example a battery, and a switch 320 supply electrical current for the processor 314 which is connected to and operates the florescence emitter 310 and the florescence detector 312.

As will be appreciated by those skilled in the art, the processor 314 preferably comprises power supplies for the florescence emitter 310, the florescence detector 312, amplifiers for the signal generated by the florescence detectors 312, analog-to-digital convertors, and a microprocessor, all represented by processor 314, which can be readily programmed using the information contained herein and in accordance with known techniques. A display 318 provides a visually readable value corresponding to the substance concentration in the amniotic fluid present between the inlet 302 and outlet 304 when the tube is placed in a corresponding channel 308 formed in the housing 306 and in which the florescence emitter 310 and the florescence detector 312 are positioned. The observation arrangement 300 can be fabricated either as a reusable unit or as a single use unit.

In view of the foregoing, it will be appreciated that the present invention's feature of using visual detection only or a combination of machine detection and visual detection, or machine detection only, provides advantages not previously available in the industry. The present invention also provides a more efficient, easy-to-use, and cost effective system for detection of a biological substance in amniotic fluid during labor and delivery. The present invention also provides a system for measurement of meconium during labor and delivery which can also measure one or more additional fetal or maternal physiological parameters, such as intrauterine pressure. The present invention further provides a system for detection of meconium staining of amniotic fluid which provides both visual and automated detection of meconium and which can be routinely employed in all labor and delivery procedures.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system for intrauterine detection of at least one biological substance, the system comprising:
   first lumen means for providing a first lumen, the first lumen means having a first port located at a distal end of the first lumen means and also having a proximal end;
   means for inserting the first port and at least a portion of the first lumen means into a uterus;
   means for drawing a fluid sample from the uterus into the first port and into the first lumen means up to the proximal end of the first lumen means; and
   means connected to the proximal end for observing the fluid sample drawn up to the proximal end of the first lumen means such that the presence of the biological substance of the fluid can be detected.

2. A system for intrauterine detection of a selected biological substance as defined in claim 1 further comprising:
   a pressure transducer having a diaphragm with first and second sides, the pressure transducer positioned on the first lumen means;
   means for communicating any pressure pulses from the fluid to the first side of said diaphragm;
   means for venting the second side of said diaphragm to atmospheric pressure; and
   electrical conductor means for electrically connecting the pressure transducer to a monitor device for displaying data corresponding to pressure sensed by said pressure transducer.

3. A system for intrauterine detection of a selected biological substance as defined in claim 2 further comprising:
   protective cushion means for protecting the uterus, the protective cushion means positioned at a proximal end of the first lumen means for providing at least a first lumen; and
   means for imparting a desired degree of rigidity to the means for providing at least a first lumen to facilitate insertion of said means for providing a first lumen into a uterus.

4. A system for intrauterine detection of a selected biological substance as defined in claim 1 wherein the first lumen means comprises means for providing a first lumen and a second lumen.

5. A system for intrauterine detection of a selected biological substance as defined in claim 1 further comprising means for infusing a fluid into the first lumen means and through the first port and into the uterus.

6. A system for intrauterine detection of a selected biological substance as defined in claim 1 further comprising:
   second lumen means for providing a second lumen, the second lumen means having a second port located at a distal end of the second lumen means; and
   means for infusing fluid into the uterus through the second lumen means and the second port.

7. A system for intrauterine detection of a selected biological substance as defined in claim 1 wherein the selected biological substance is at least one substance selected from the group consisting of meconium and blood.

8. A system for intrauterine detection of a selected biological substance as defined in claim 1 wherein the means for drawing fluid from the uterus into the first port and into the first lumen means comprises a syringe.

9. A system for intrauterine detection of a selected biological substance as defined in claim 8 wherein the means for drawing fluid from the uterus into the first port into the first lumen means further comprises:
   a first connector joined to the proximal end of the first lumen means; and
   a second connector joined to the syringe, the first connector and the second connector forming a removable fluid tight connection therebetween.

10. A system for intrauterine detection of a selected biological substance as defined in claim 1 wherein the means for observing the fluid sample comprises a transparent cuvette in fluid communication with the means for providing a first lumen.

11. A system for intrauterine detection of a selected biological substance as defined in claim 1 wherein the means for observing the fluid sample comprises:
   means for holding a volume of the fluid;
   viewing means for observing the appearance of the fluid in the means for holding the fluid; and
   means for illuminating the interior of the means for holding such that at least any threshold amount of meconium present in the fluid can be observed, the means for illuminating comprises means for providing an illumination spectrum which is suited for detection of meconium in amniotic fluid.

12. A system for intrauterine detection of a selected biological substance as defined in claim 11 wherein the means for illuminating comprises a white light source.

13. A system for intrauterine detection of a selected biological substance as defined in claim 11 further comprising a color reference chart illuminated by the means for illuminating.

14. A system for intrauterine detection of a selected biological substance as defined in claim 1 wherein the means for observing the fluid sample comprises:
- means for holding a volume of the fluid, wherein the means for holding comprises a transparent tube;
- viewing means for observing the appearance of the fluid in the means for holding the fluid; and
- means for illuminating the interior of the means for holding such that at least a threshold amount of meconium present in the fluid can be observed, the means for illuminating comprises means for providing an illumination spectrum which is suited for detection of meconium in amniotic fluid.

15. A system for intrauterine detection of a selected biological substance as defined in claim 1 wherein the means for observing the fluid sample comprises:
- means for holding a volume of the fluid, the means for holding being tubular and transparent and having an exterior; and
- a plurality of visually perceptible reference patches formed on the exterior of the means for holding, the plurality of visually perceptible reference patches representing different expected appearances of the fluid.

16. A system for intrauterine detection of a selected biological substance as defined in claim 1 wherein the means for observing the fluid sample comprises:
- means for holding a volume of the fluid, the means for holding being tubular and transparent and having an exterior; and
- a substantially visually neutral surface adjacent to the means for holding;
- means for securing the means for holding next to the substantially visually neutral surface; and
- a plurality of visually perceptible reference patches formed on the visually neutral surface, the plurality of visually perceptible reference patches representing different expected appearances of the fluid.

17. A system for intrauterine detection of a selected biological substance as defined in claim 1 wherein the means for observing the fluid sample comprises:
- means for holding a volume of the fluid, the means for holding being tubular and transparent and having an exterior; and
- a substantially visually neutral surface adjacent to the means for holding;
- means for securing the means for holding next to the substantially visually neutral surface;
- means for illuminating the interior of the means for holding;
- a plurality of visually perceptible reference patches formed on the visually neutral surface, the plurality of visually perceptible reference patches being at least translucent and representing different expected appearances of the fluid; and
- means for passing any light in the interior of the means for holding through at least some of the plurality of the visually perceptible transparency reference patches such that the visually perceptible transparency reference patches are backlit.

18. A system for intrauterine detection of a selected biological substance as defined in claim 1 wherein the means for drawing fluid from the uterus into the first port and into the means for providing the first lumen means comprises a syringe and wherein the means for observing comprises a syringe body and a plurality of visually perceptible reference patches formed on the syringe body, the plurality of visually perceptible reference patches representing different expected appearances of the fluid.

19. A system for intrauterine detection of a selected biological substance as defined in claim 1 wherein the means for observing the fluid sample comprises:
- first means for holding a volume of the fluid;
- viewing means for observing the appearance of the fluid in the means for holding the fluid;
- first means for illuminating the interior of the first means for holding such that at least a threshold amount of meconium present in the fluid can be observed;
- second means for holding a volume of the fluid;
- photo emitter means for emitting radiation into the second means for holding any fluid contained therein, the photo emitter means emitting radiation at a first wavelength;
- photo detector means for perceiving the radiation at the first wavelength absorbed by the fluid in the second means for holding; and
- means for indicating in a humanly perceptible manner the detection of meconium in the fluid in accordance with the absorption of the radiation at the first wavelength.

20. A system for intrauterine detection of a selected biological substance as defined in claim 1 wherein the means for observing the fluid drawn up to the proximal end of the means for providing a lumen comprises:
- first means for holding a volume of the fluid;
- viewing means for observing the appearance of the fluid in the means for holding the fluid;
- first means for illuminating the interior of the first means for holding such that at least a threshold amount of meconium present in the fluid can be observed;
- second means for holding a volume of the fluid;
- first photo emitter means for emitting radiation into the second means for holding any fluid contained therein, the first photo emitter means emitting radiation at a first wavelength;
- first photo detector means for perceiving the radiation at the first wavelength absorbed by the fluid in the second means for holding;
- means for blocking the effect of the first means for illuminating on the first photo detector; and
- means for indicating in a humanly perceptible manner the detection of meconium in the fluid in accordance with the absorption of the radiation at the first wavelength.

21. A system for intrauterine detection of a selected biological substance as defined in claim 1 wherein the means for observing the fluid sample comprises:
- means for holding a volume of the fluid;
- emitter means for emitting radiation into the means for holding, the emitting means emitting radiation at a wavelength causing the selected biological substance to fluoresce;
- fluorescence detector means for perceiving the fluorescence emitted from the means for holding; and
- means for indicating in a humanly perceptible manner the detection of the biological substance contained in the means for holding.

22. A system for reducing the effect of at least one undesirable biological substance in a uterus, the system comprising:
- first lumen means for providing at least a first lumen, the first lumen means having a first port located at a distal end of the lumen and also having a proximal end;

means for inserting the first port and at least a portion of the first lumen means into the uterus;

means for drawing a fluid sample from the uterus into the first port and into the first lumen means up to the proximal end of the first lumen means;

means connected to the proximal end for observing the fluid sample drawn up to the proximal end of the first lumen means such that the presence of the biological substance in the fluid can be detected;

means for withdrawing fluid from the first lumen means; and means for infusing an infused fluid into the uterus.

23. A system as defined in claim 22 further comprising:

second lumen means for providing a second lumen, the second lumen means having a second port located at a distal end of the second lumen means; and means for infusing fluid into the uterus through the second lumen means and the second port.

24. A system as defined in claim 22 wherein the undesirable biological substance is at least one substance selected from the group consisting of meconium and blood.

25. A system for intrauterine detection of a selected biological substance as defined in claim 22 wherein the means for drawing fluid from the uterus into the first port and into the first lumen means comprises a syringe.

26. A system for intrauterine detection of a selected biological substance as defined in claim 22 wherein the means for infusing fluid comprises:

second lumen means for providing a second lumen, the second lumen means having a second port located at a distal end of the second lumen means; and a syringe connected to the second lumen means.

27. A method for intrauterine detection of a selected biological substance comprising the steps of:

providing at least a first lumen, the first lumen having a first port located at a distal end of the lumen and also having a proximal end of the lumen;

inserting at least a portion of the first lumen and the first port into a uterus;

drawing a fluid sample from the uterus into the first port and into the proximal end of the first lumen; and observing the fluid sample at the proximal end such that the presence of the biological substance in the fluid can be detected.

28. A method for intrauterine detection of a selected biological substance as defined in claim 27 further comprising the steps of:

providing a pressure transducer having a diaphragm with first and second sides, the pressure transducer positioned on the first lumen more than half-way toward the distal end;

communicating any pressure pulses from the fluid to the first side of said diaphragm;

venting the second side of said diaphragm to atmospheric pressure; and electrically connecting the pressure transducer to a monitor device for displaying data corresponding to pressure sensed by said pressure transducer.

29. A method for intrauterine detection of a selected biological substance as defined in claim 28 further comprising the steps of:

providing a protective cushion positioned at a distal end of the first lumen; and imparting a desired degree of rigidity to the first lumen to facilitate insertion of said first lumen.

30. A method for intrauterine detection of a selected biological substance as defined in claim 27 wherein the step of providing at least a first lumen comprises the step of providing a first lumen and providing a second lumen.

31. A method for intrauterine detection of a selected biological substance as defined in claim 27 wherein the step of drawing fluid from the uterus into the first port and into the first lumen comprises the step of creating a vacuum in the first lumen.

32. A method for intrauterine detection of a selected biological substance as defined in claim 31 wherein the step of drawing fluid from the uterus into the first port and into the first lumen further comprises the steps of:

providing a syringe;

joining a first connector to the proximal end of the first lumen; and joining a second connector to the syringe, the first connector and the second connector forming a removable fluid tight connection therebetween.

33. A method for intrauterine detection of a selected biological substance as defined in claim 27 wherein the step of observing the fluid drawn up to the proximal end of the first lumen comprises the step of providing a transparent cuvette in fluid communication with the first lumen.

34. A method for intrauterine detection of a selected biological substance as defined in claim 27 wherein the step of observing the fluid drawn up to the proximal end of the lumen comprises the steps of:

holding a volume of the fluid;

viewing the appearance of the fluid as the fluid is held; and illuminating the volume of fluid being held such that at least any threshold amount of meconium present in the fluid can be observed.

35. A method for intrauterine detection of a selected biological substance as defined in claim 34 wherein the step of illuminating the volume of fluid comprises the step of illuminating the volume of fluid with a white light source.

36. A method for intrauterine detection of a selected biological substance as defined in claim 34 further comprising the step of comparing the appearance of the volume of fluid to a color reference chart.

37. A method for intrauterine detection of a selected biological substance as defined in claim 27 wherein the step of observing the fluid drawn up to the proximal end of the lumen comprises:

holding a volume of the fluid in a transparent tube;

viewing the appearance of the fluid as the fluid is held; and illuminating the volume of fluid such that at least a threshold amount of meconium present in the fluid can be observed.

38. A method for intrauterine detection of a selected biological substance as defined in claim 27 wherein the step of observing the fluid drawn up to the proximal end of the lumen comprises the steps of:

holding a first volume of the fluid;

viewing the appearance of the first volume of fluid;

illuminating the first volume of fluid such that at least a threshold amount of meconium present in the first volume of fluid can be observed;

holding a second volume of the fluid;

emitting radiation at a first wavelength into the second volume of fluid;

detecting the radiation at the first wavelength absorbed by the second volume of fluid; and indicating in a humanly perceptible manner the detection of meconium in the second volume of fluid in accordance with the absorption of the radiation at the first wavelength.

39. A method for intrauterine detection of a selected biological substance as defined in claim 27 wherein the means for observing the fluid drawn up to the proximal end of the lumen comprises:

holding a first volume of the fluid;

viewing the appearance of the first volume of fluid; illuminating the first volume of fluid such that at least a threshold amount of meconium present in the first volume of fluid can be observed;

holding a second volume of the fluid;

emitting radiation at a first wavelength into the second volume of fluid;

detecting the radiation at the first wavelength absorbed by the second volume of fluid;

blocking the effect of the illumination of the first volume of fluid on the detection of the radiation at the first wavelength absorbed by the second volume of fluid; and indicating in a humanly perceptible manner the detection of meconium in the second volume of fluid in accordance with the absorption of the radiation at the first wavelength.

40. A method for intrauterine detection of a selected biological substance as defined in claim 27 wherein the step of observing the fluid comprises the steps of:

emitting radiation at a first wavelength into the first volume of fluid;

detecting the florescence of the biological substance in the first volume of fluid; and indicating in a humanly perceptible manner the detected florescence.

41. A system for detection of a selected biological substance during labor and delivery of a human fetus and for monitoring at least one maternal/fetal physiological parameter, the system comprising:

cable means for providing an elongated member for insertion into a body cavity and including a first lumen positioned therein, the cable means comprising a proximal end and a distal end;

means for sensing a first physiological parameter at least partially positioned at the distal end of the cable means and for generating a first signal representing the first physiological parameter;

conductor means for conveying the first signal to the proximal end of the cable means;

a first port located at the distal end of the cable means and connected to the first lumen;

means for drawing fluid from the uterus into the first port and into the first lumen to obtain a fluid sample; and means connected to the proximal end for observing the fluid sample such that the presence of any biological substance selected from the group consisting of meconium and blood in the fluid can be detected.

42. A system for detection of a selected biological substance during labor and delivery of a human fetus as defined in claim 41 wherein the means for sensing a first physiological parameter comprises a pressure transducer and wherein the conductor means for conveying the first signal comprises a plurality of electrical conductors.

43. A system for detection of a selected biological substance during labor and delivery of a human fetus as defined in claim 41 wherein the means for drawing fluid from the uterus into the first port and into the first lumen comprises a syringe.

44. A system for detection of a selected biological substance during labor and delivery of a human fetus as defined in claim 41 wherein the means for observing the fluid comprises a transparent holder.

45. A system for detection of a selected biological substance during labor and delivery of a human fetus as defined in claim 41 wherein the means for observing the fluid comprises:

a photo emitter positioned to emit radiation into the fluid;

a photo detector for detecting the absorption of the radiation by the fluid; and means for indicating in a humanly perceptible manner the detection of the selected biological substance in accordance with the absorption of the radiation.

* * * * *